(12) United States Patent
Sallaz et al.

(10) Patent No.: US 10,869,677 B2
(45) Date of Patent: Dec. 22, 2020

(54) INTEGRATED INTRAOPERATIVE NERVE MONITORING SYSTEM

(71) Applicant: Bien-Air Holding SA, Bienne (CH)

(72) Inventors: Adrian Sallaz, Grenchen (CH); Roman Amrein, Biel/Bienne (CH)

(73) Assignee: BIEN-AIR HOLDING SA, Bienne (CH)

( * ) Notice: Subject to any disclaimer, the term of this patent is extended or adjusted under 35 U.S.C. 154(b) by 0 days.

(21) Appl. No.: 16/096,180

(22) PCT Filed: May 3, 2017

(86) PCT No.: PCT/EP2017/060565
§ 371 (c)(1),
(2) Date: Oct. 24, 2018

(87) PCT Pub. No.: WO2017/191206
PCT Pub. Date: Nov. 9, 2017

(65) Prior Publication Data
US 2019/0133609 A1 May 9, 2019

(30) Foreign Application Priority Data

May 3, 2016 (EP) ..................... 16168034

(51) Int. Cl.
*A61B 17/16* (2006.01)
*A61B 5/04* (2006.01)
(Continued)

(52) U.S. Cl.
CPC ...... *A61B 17/1626* (2013.01); *A61B 5/04001* (2013.01); *A61B 5/4893* (2013.01);
(Continued)

(58) Field of Classification Search
CPC ..................... A61B 17/16–17/1697
See application file for complete search history.

(56) References Cited

U.S. PATENT DOCUMENTS 7,717,932 B2 * 5/2010 McFarlin ........... A61B 17/1622
606/170
7,878,981 B2 * 2/2011 Strother ............ A61B 5/04001
600/554

(Continued)

FOREIGN PATENT DOCUMENTS

| DE | 102012018032 A1 | 5/2014 |
| EP | 2166937 A2 | 3/2010 |
| WO | 2005074831 A2 | 8/2005 |

OTHER PUBLICATIONS

International Search Report & Written Opinion issued in corresponding application No. PCT/EP2017/060565 dated Oct. 5, 2017, 11 pages.

*Primary Examiner* — Zade Coley
(74) *Attorney, Agent, or Firm* — Pearne & Gordon LLP

(57) ABSTRACT

A surgical drilling device (10) with integrated nerve monitoring capabilities comprising a bur (1) fitted with a drilling tip (12), and that is actuated in rotation by a rotating shaft (11) driven by a motor (5) wherein the rotating shaft (11) is electrically connected at a rear end (11B) thereof to a coupling device (21) of a nerve monitoring module (20) for the transmission of electrical nerve stimulation signals (S) through axial contacting.

19 Claims, 4 Drawing Sheets

(51) Int. Cl.
  *A61B 5/00* (2006.01)
  *A61N 1/36* (2006.01)
  *A61B 17/00* (2006.01)
  *A61B 90/00* (2016.01)

(52) U.S. Cl.
  CPC ........ *A61B 5/6847* (2013.01); *A61B 17/1615* (2013.01); *A61B 17/1622* (2013.01); *A61B 17/1679* (2013.01); *A61N 1/36* (2013.01); *A61B 2017/00039* (2013.01); *A61B 2017/00119* (2013.01); *A61B 2017/00132* (2013.01); *A61B 2017/00154* (2013.01); *A61B 2090/08021* (2016.02); *A61B 2505/05* (2013.01)

(56) References Cited

U.S. PATENT DOCUMENTS

| | | | | |
|---|---|---|---|---|
| 7,896,815 B2* | 3/2011 | Thrope | ............... | A61B 5/05 600/554 |
| 8,016,846 B2* | 9/2011 | McFarlin | ........... | A61B 5/04001 606/170 |
| 8,052,688 B2* | 11/2011 | Wolf, II | ............... | A61B 5/0488 606/104 |
| 8,172,768 B2* | 5/2012 | Strother | ............. | A61B 17/1626 600/554 |
| 8,241,313 B2* | 8/2012 | McFarlin | ........... | A61B 17/1622 606/170 |
| 8,758,378 B2* | 6/2014 | McFarlin | ........... | A61B 5/04001 606/170 |
| 2007/0100334 A1* | 5/2007 | McFarlin | ........... | A61B 17/1622 606/45 |
| 2007/0100336 A1* | 5/2007 | McFarlin | ........... | A61B 5/04001 606/45 |
| 2007/0191915 A1* | 8/2007 | Strother | ............. | A61B 17/8875 607/63 |
| 2007/0239187 A1* | 10/2007 | Brunnett | ............ | A61B 17/1622 606/172 |
| 2008/0262526 A1* | 10/2008 | Neubardt | ........... | A61B 17/1615 606/180 |
| 2009/0138050 A1* | 5/2009 | Ferree | ................ | A61B 17/1626 606/279 |
| 2009/0299439 A1* | 12/2009 | Mire | .................. | A61B 17/1626 607/60 |
| 2010/0179557 A1* | 7/2010 | Husted | ............ | A61B 17/32002 606/83 |
| 2010/0198219 A1* | 8/2010 | McFarlin | ........... | A61B 17/1622 606/45 |
| 2012/0004680 A1* | 1/2012 | McFarlin | ........... | A61B 5/04001 606/170 |
| 2012/0143084 A1* | 6/2012 | Shoham | ........... | A61B 17/1675 600/567 |
| 2013/0060278 A1* | 3/2013 | Bozung | ................. | A61B 34/20 606/205 |
| 2013/0245704 A1* | 9/2013 | Koltz | ............. | A61B 17/1626 606/86 A |
| 2014/0073985 A1* | 3/2014 | Sakai | .................. | A61B 5/4887 600/554 |
| 2015/0119874 A1* | 4/2015 | Brunnett | ............ | A61B 17/1622 606/39 |
| 2015/0164527 A1* | 6/2015 | Maier | .................... | B23Q 15/10 700/160 |

* cited by examiner

INTEGRATED INTRAOPERATIVE NERVE MONITORING SYSTEM

TECHNICAL FIELD

The invention relates to the field of intraoperative neurophysiological monitoring (IONM). In particular, but not exclusively, it relates to a fast spinning drill with integrated nerve detection apparatus meant for ear-nose-throat (ENT) surgeries.

BACKGROUND

Intraoperative nerve monitoring systems allow nerves in the body to be located, and are used to reduce the risk of damage to the nerves during operation.

Since drilling is an indispensable need during ear-nose-throat (ENT) surgeries, depending on the anatomic location, there is a severe risk of irreparably damaging nerves, which could lead to serious physical and mental consequences for the patient's life. Therefore, surgeons make use of stimulation probes for nerve monitoring in order to minimize that risk.

However, the use of dedicated probes is neither practical nor efficient, since a tool change between the drill and the probe is needed. As a result, nerve monitoring is not continuous, and the drilling operation is not performed simultaneously. Therefore, it has been sought to combine a surgical drilling machine with an electrical stimulation probe in one single instrument, in order to allow the surgeon to monitor nerves while drilling without changing tools. As a result, continuous nerve monitoring leads to improved safety for the patient, more confidence for the surgeon, and savings in terms of time and costs. Applications of nerve monitoring are numerous, and can be found in many surgical fields such as spinal surgery or otoneurology.

Nerve monitoring has been used and further developed for more than 20 years now, in particular in Germany and in the US, especially for observing the nervus facialis or facial nerve. Its principle is to minimize the risk of structural and functional neural damage by an early warning to the surgeon, as soon as he approaches a nerve within a certain distance. The general working principle of an intraoperative nerve monitoring system (IONM) can be described as follows: during the surgery, the surgeon has the possibility to observe critical areas, where a lot of neural structures might be involved, with an electrical stimulation probe. The tip of this probe is applied on the tissue or on the bony structure of interest. During the contacting, short harmless electrical pulses are sent into the body. If the stimulation probe is close enough to a nerve, the electrical pulses stimulate the nerve, leading to a change of activity in the motor nerve up to the muscle. The muscle activity is subsequently recorded with electromyography (EMG) electrodes. The nerve monitoring system device finally processes and analyses these EMG signals: if the signal exceeds a certain threshold value, a warning is generated.

Nowadays one major surgical device provider seems to offer the only nerve monitoring system (a.k.a. "Stim Bur Guard") on the market with an integrated high-speed drill system. This drill system provides nerve monitoring during the drilling process, and the surgeon does not have to check anymore, using an additional stimulating probe, whether there is any dangerous neural tissue structure.

This system is a lot more convenient, and saves time because no additional measuring with the stimulation electrode is needed. The safety increase is huge, due to continuous monitoring. However, it also has some drawbacks. There is an ergonomic change on the surgical drill device because of an additional support with an extra cable. Another difficulty is signal transmission, over an electrolyte or over brushes, because no direct current is injected; hence, it is difficult to control the stimulation current and the shape of the signal.

The patent document U.S. Pat. No. 8,758,378 of Medtronic discloses an example of such a surgical drill with integrated nerve monitoring capabilities that is provided with an additional housing, and wherein an electrical conducting fluid is injected in a tubing for transmitting the signal to an electrical connector. The signal transmission between the electrical connector and the drill is solved differently in patent document EP2166937, wherein the cutting tool shank, i.e. the drill, is connected to the signal lead through a plurality of carbon wires in the form of a wire brush extending radially inwards and that is laid upon an outer peripheral wall of the shank. The signal lead, which conveys the stimulation signal sent from a remote nerve monitoring system, can thus transmit this electrical signal via the wire brush onto the cutting tool shank. Although this alternative electrical coupling through sliding contact may minimize the wear, the reliability thereof is not guaranteed under dynamic conditions of use, where the influence of vibrations may result in backlash and therefore deteriorate the contacting properties between the connector and the drill, which thus results in signal impairment, e.g. at very high rotational speeds.

Another patent document US2009/299439 describes a drilling tool provided with a neural integrity monitoring system (NIM), connected to the drill through a quick connect coupling device and an active assembly unitary with a chuck holding the drill. As a result, still a sliding contact seems to be necessary, e.g. through a slipping ring rotatable along the rotation axis of the drill, in order to ensure a reliable galvanic contact between the rotating drill and the fixed electrical connecting part. As a result, much friction may be generated that can lead to significant heating and fast wearing, hence deteriorating the overall performances and lifetime, especially when high rotating speeds are applied (several tens of thousands of rotations per minute). Patent document US2014/0073985 similarly describes a stimulation device used with a drilling or screwing device, wherein an electrode performing the drilling is secured to the device with the help of a chuck, and then electrically connected to an integrated stimulation control device through an internal lead, for which the exact same problems may arise.

Another patent document DE102012018032 from Inomed GmbH describes a surgical electrical stimulation device intended for use in drilling, milling and cutting procedures, wherein the transmission of electrical stimulation current to the drill tip is based on a capacitive principle instead of resistive coupling, and therefore does not require any actual physical contact anymore. Such a solution involves for example a rotatory capacitor with a fixed outer part connected to a nerve monitor system and an inner part that is the cutting tool shank. Despite the fact that the contactless properties of such a solution mean an absence of wear and therefore could lead to a potentially unlimited lifetime for the provided nerve monitoring system, a critical issue that arises with such a solution is the difficulty to transmit an arbitrary signal shape with enough power due to the reduced size of the capacity. Indeed, the cylindrical capacitor modelling involving the length and logarithmic ratio of the two radii of each electrode, combined with the relationship between the current intensity and the derivative function of the voltage, shows that a huge amount of space would be required for the embedded capacitor in order to reach a capacity that would be high enough in order to transmit a current of suitable intensity, without yet yielding consequently too high voltages, i.e. far above the breakdown voltage. As a result, in view of the average dielectric strength of air and the available spacing between the two electrodes, there would hence be a need for an appropriate dielectric material leading to increased capacities up to tens of nanofarads instead of currently tens of picofarads for usual surgical drills of a regular size to be allowed for medical implementation, where voltages are required not to exceed 50 volts to get clinical admission. Such dielectrics are not available so far.

Moreover, a further challenge of the capacitive principle is the absolute sealing of the capacitor, because the presence of any fluid or even humidity between the electrodes would dramatically alter the dielectric properties, and may shortcut the capacitor that would eventually be irreparably damaged, whereby the patient's tissue would be subjected to severe risk if this happened while stimulating.

As another contactless coupling option, inductive coupling solutions have also been considered; yet a limitation thereof is the necessity to develop a bipolar bur in order to transmit the stimulation signal, since any coil has two ends which need to be contacted. This proved to be quite expensive. Moreover, the coil coupling makes it difficult to drive specific electrical signal shapes, and the balancing of the numerous electrical components requires a lot of time and effort, especially for fast spinning drills driven at over 80,000 revolutions per minute (rpm), which generate substantial centrifugal forces.

There is hence a need for an integrated nerve monitoring system free from all these known limitations.

SUMMARY

The present invention is aimed at offering an optimized system combining a surgical drilling machine and a nerve detection electrode into one single product, allowing a surgeon to monitor nerves reliably in real time while drilling at a very high rotation speed.

Another goal of the present invention is to provide an integrated nerve detection probe with an extended lifetime.

To this end, the present invention concerns a surgical drilling device with integrated nerve monitoring capabilities comprising a bur fitted with a drilling tip, and that is actuated in rotation by a rotating shaft, wherein the rotating shaft is electrically connected at its rear end to a coupling device of a nerve monitoring module comprising an axial contacting element for the transmission of electrical nerve stimulation signals through a contacting surface stretching inside the radius of the rear end of the rotating shaft.

The present invention concerns also a system for operating such a surgical drill, wherein the nerve detection module further comprises a remote control unit that is configured to send electrical pulse signals to said coupling device for generating intermittent electrical contact between said coupling device and said rotating shaft.

An advantage conferred by the claimed solution is that the contacting principle along the rotation axis requires a much smaller contact length in dynamic situations as compared with the known radial sliding contact principle in order to provide comparable reliability. As a result, the friction is minimized and thus accordingly the wear of the pieces in contact with each other.

The reduced size required for the physical contact yielding the resistive electrical conductivity also allows for a compact and ergonomic design of the provided completed surgical drill, in which the nerve monitoring part can easily be integrated without significant changes of the casing shape and size, hence not impacting the surgeon's habits in any manner. Moreover, it is also possible to reuse all existing internal functional parts of an available drilling device including a regular unipolar bur and its actuating motor; only a small additional apparatus needs to be plugged inside a rear end of the casing. Such a modular design makes it possible to leverage existing manufacturing platform tools and know-how and hence significantly reduce the marginal production costs. It can further be appreciated that no additional external cabling is required to transmit the stimulation signals up to the tip of the bur, unlike the existing nerve monitoring solutions.

A further advantage of the coupling scheme proposed within the framework of the present invention is that all kinds of signal shapes can be efficiently transmitted over the provided mechanical contact without any additional settings, i.e. the drilling tool can still be used within the same range of rotational speeds, and the usual electrical nerve stimulation pulses can still be employed, which spares unnecessary changes in the back-end controlling infrastructure as well. The provided resistive contact also allows enough power to be transmitted up to the tip of the probe.

In order to further minimize the wear, which generates heat and polluting particles that in turn greatly reduce the lifetime, it is proposed to operate the claimed surgical drill so as to provide a pulsed mechanical contact between the rotating shaft of the bur and the coupling device of the nerve monitoring module. To this end, according to a preferred embodiment of the present invention, a linear actuator is displaced axially according to a pulsed pattern that is intended to reduce the contact time as much as possible in order to minimize the wear. This pattern is structured around the shape and frequency of the nerve stimulation signals in order to still guarantee the quality of the electrical transmission while addressing the wear issue.

Further advantageous features aimed at optimizing the nature of the mechanical contact, specifying a preferred layout for the linear actuator applied for the intermittent contacting scheme and defining adjustments of the sent electrical pulses in order to always ensure a reliable physical contact are discussed in the following detailed description, with reference to the drawings illustrating preferred embodiments for the present invention.

BRIEF DESCRIPTION OF THE DRAWINGS

The invention will now be described in greater detail with reference to accompanying figures, in which.

DETAILED DESCRIPTION

In the following, a preferred system and method will be described to allow for the transmission of electrical pulses through an operating drilling system comprising a bur running at very high speed (possibly up to 120,000 rpm), with limited wear or heat generation, while also transmitting nerve stimulation signals up to the tip of the bur during a surgical operation.

Figures 1, 1A, 1B:
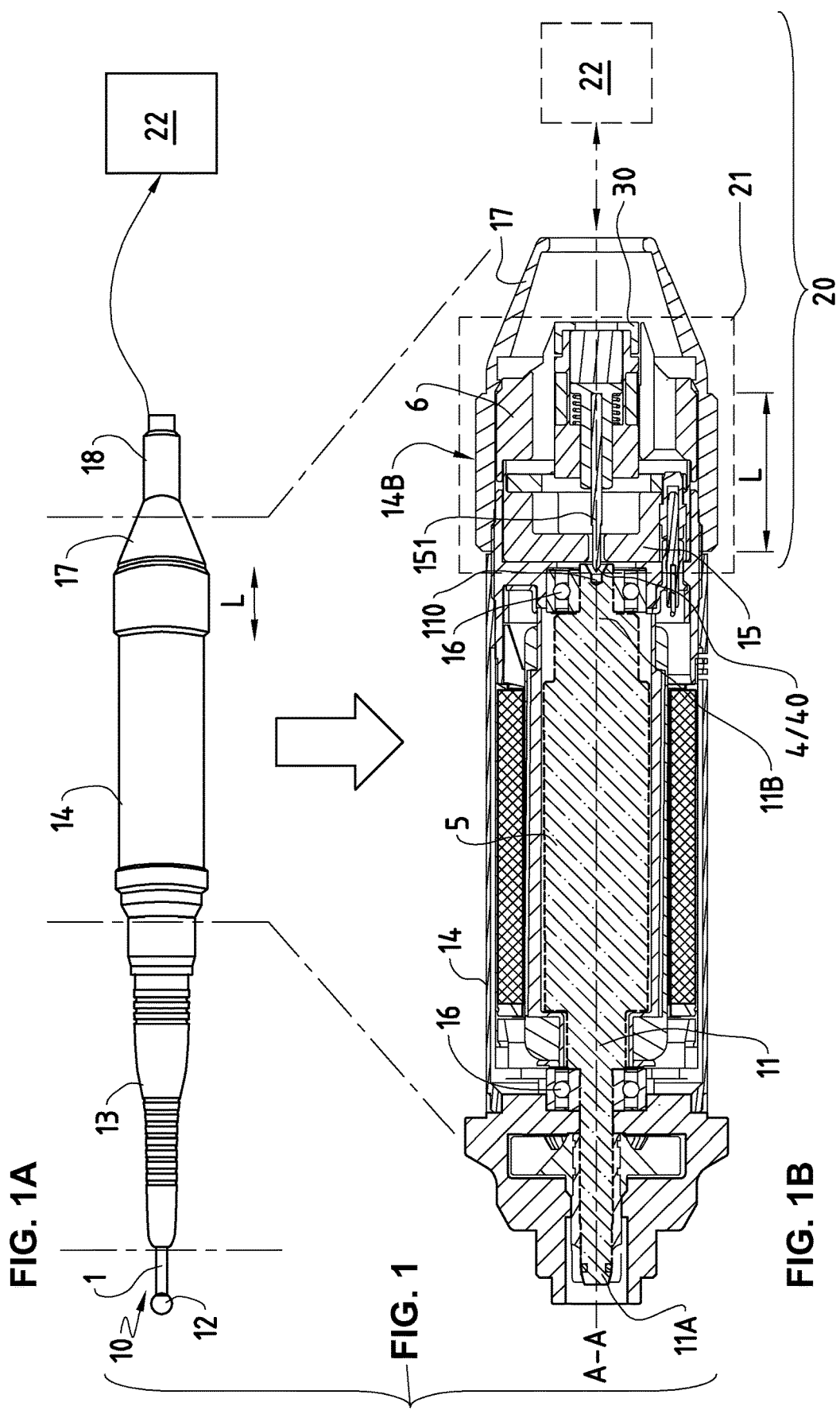
FIG. 1 consists of FIGS. 1A and 1B showing respectively a side perspective view of a surgical drilling device with integrated nerve detection, and an enlarged sagittal cross-sectional view of the inner casing part thereof according to a preferred embodiment of the present invention; the rightmost part of FIGS. 1A and 1B is supplemented by a box representing a remote control unit for the device.

FIG. 1 is composed of a first upper FIG. 1A, whose purpose is to show how the new proposed surgical drill fits into an existing product of the applicant with minimal ergonomic changes, and a lower FIG. 1B showing how the integration of the new parts relating to the nerve detection module is achieved, thereby hinting at the new proposed axial contacting scheme for the built-in coupling device.

FIG. 1A thus shows a surgical drill 10 of usual appearance and size, comprising a bur 1 fitted with a drilling tip 12 driven in rotation by, and preferably integral with, a rotating shaft 11. Most of the bur 1 is concealed under a part commonly referred to as "handpiece" 13, because it is the part actually held by the surgeon during an operation. The rotating shaft 11 is actuated in rotation by a motor 5—visible in FIG. 1B only—mounted inside the casing 14. The motor 5 is supplied with electrical power, and to this end a connexion cable 18 is provided at the back end of the casing 14, opposite to the side where the bur 1 is mounted and the handpiece 13 is attached; the cabling inside the casing 14 is covered by a so-called protection cap 17. On the right-hand side of FIG. 1A is depicted a box representing a remote control unit 22 connected to the surgical drill 10. This unit is part of the nerve monitoring module, which does not primarily function alone in an autonomous way inside the surgical drill 10. The full nerve monitoring module 20 is actually shown in FIG. 1B, where it can be appreciated that it is made up of this remote control unit 22 and a built-in coupling device 21 embedded in the motor casing 14. This remote control unit 22 can typically be used to send electrical stimulation signals, as explained hereinafter, and it preferably comprises also a display for providing real-time visual feedback during operation. This unit, that hence preferably consists not of one single, but actually several, physical electronic modules, could be integrated in a larger remote monitoring and command platform controlling all the operations performed by the surgical drill.

FIG. 1A highlights the fact that preferably only a small extra length L, typically comprising between 5 mm and 10 mm, is necessary for the new proposed surgical drill 10 with integrated nerve monitoring capabilities, as compared with a regular surgical drill 10. This extra length L can be provided by the casing 14 itself, or alternatively and as illustrated, through an extra ring of the same extra length L. As a result, the external appearance and functional design of the new surgical drill is practically unchanged, with merely a small added length, not exceeding 10 mm, of its main body made up by the motor casing 14. What is more important, from a surgeon's perspective, is that the handpiece part 13 is left completely untouched, so that the best possible ergonomics is still ensured despite the integration of this new nerve monitoring feature. According to an alternative embodiment, it could even be foreseen to have no added length at all for the casing 14 as compared with a regular surgical drill 10 by slightly shortening the length of the other embedded motor parts.

Figure 3:
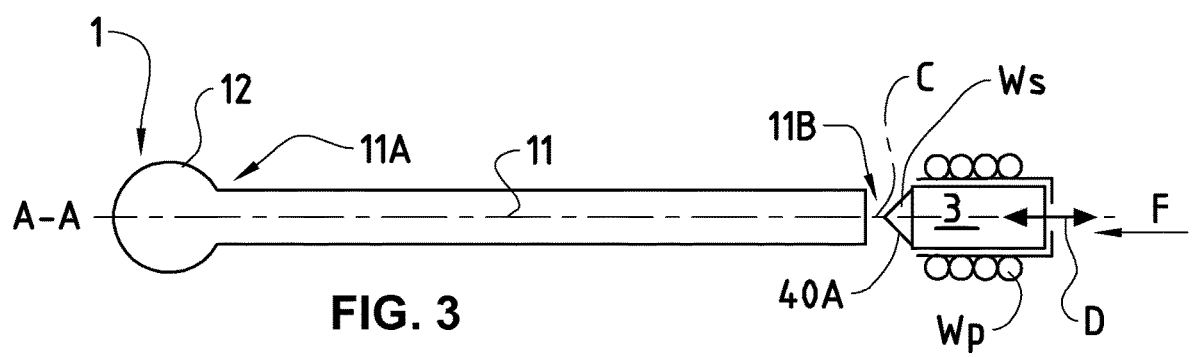
FIG. 3 shows a schematic view illustrating the operating principle between a bur and a linear actuator intended for sporadic electrical contacting as used within the framework of a preferred embodiment of the present invention.

FIG. 1B is an enlarged cross-sectional view in a sagittal plane of the motor casing 14 part of the surgical drill 10 of FIG. 1A, showing all internal parts housed therein and putting forward the modular mounting structure of the added coupling device 21 for setting up the nerve monitoring module capability. It shows the rotating shaft 11, arranged centrally inside the casing 14, and that is rotatable around its rotational axis A-A. A main body of the rotating shaft 11 is radially surrounded by a motor 5, typically an electromechanical motor. At both ends of the motor 5, bearings 16 are foreseen to hold the rotating shaft 11 axially and radially, with only one degree of freedom in rotation around the rotational axis A-A. According to the illustrated preferred embodiment of FIG. 1B, the bur 1, which is not illustrated on this figure, is releasably coupled to the distal end 11A of the rotating shaft 11 main body. In other words, the rotating shaft 11 consists here of two parts: a main body driven by the motor 5, and an auxiliary arm made up by shaft of the bur 1 itself. As a result, the bur 1 has a rotating shaft of reduced length and may then be used as a wearing part that can be interchanged without needing to access a main body part rigidly coupled to the motor 5. According to a variant embodiment, however, the rotating shaft 11 could be made up of a single monobloc unit whose distal end 11A would stretch up to the drilling tip 12 of the bur 1. Such a variant embodiment is schematically illustrated in FIG. 3.

The mounting of the usual internal pieces pertaining to the surgical drill 10 including the motor 5 and the rotating shaft 11 is achieved in a modular fashion inside the casing 14 wherein a stand-alone module is accommodated towards the front end thereof. Beyond this module, some additional axial space is generated towards the back end 14B of the casing 14 in order to fit in a coupling device 21 for the nerve monitoring module 20. The module containing all motor parts is closed beyond the rear end 11B of the rotating shaft 11 by a spacer 15, taking preferably the form of a cylindrical casing ring or a sleeve, onto which is fitted a plug 6 inside which is arranged an electromechanical linear actuator 30. This electromechanical linear actuator 30, whose constituent parts are described in detail further in FIG. 4 hereinafter, is guided in translation along the rotational axis A-A of the rotating shaft 11, by the plug 6 and is equipped, towards its distal end, with an axial contacting element 4, here made of a contacting pin 40 in order to provide a mechanical contact with the rotating shaft 11, and, as a result, provide resistive electrical conductivity in order to transmit electrical signals generated by the remote control unit 22. The contacting pin 40 is preferably terminated with a sharp tip 40A coming across a central opening 151 of the spacer 15 to contact the rear end 11B of the rotating shaft 11, which shows a recess 110, preferably of a conical shape as illustrated, in order to receive the sharp tip 40A of the contacting pin 40. Such a layout is intended to minimize the wear during operation and ease the assembly, as explained in detail later with reference to FIG. 3.

FIG. 1B highlights the modular layout conferred by the preferred illustrated embodiment not only for the regular motor parts, but also for the built-in coupling device 21, fitted towards the back end 14B of the casing 14. In order to implement the nerve monitoring capabilities on the surgical device 10, it is only necessary to introduce the spacer 15 beyond the rotating shaft 11 through the back end 14B of the casing 14, and then mount the plug 6 fitted with the electromagnetical linear actuator 30—or any kind of linear actuator 3—onto it, and then cover this whole added new module under the added length L of an extended removable cable protection cap 17. This way, it is possible to reuse all existing internal parts of a usual motor module and just add the coupling device 21 as an additional module concealed under the additional axial added length L formed by the extended part of the removable cable protection cap 17, as illustrated, or, alternatively, achieved by an additional ring. In order to ease the assembling and disassembling operations for this alternative embodiment involving a separate ring, it would be possible to use preferably a double threaded ring, which would then be attached on one side to the back end 14B casing 14, and on the other side to a regular cable protection cap 17. As a result, as seen from the outside, the only additional part required for applying the invention is either an extended part of the removable cable protection cap 17, or an added ring, and all other parts could be reused in their original size and shape; moreover, as far as internal parts are concerned, only an additional module is integrated without impacting the remaining existing structure of the surgical device 10.

The modular configuration of the coupling device 21 also fits in very well with the usual master-slave control pattern architecture of a usual surgical device 10, that is usually at least partially remotely controlled. Here, the coupling device 21 consists of the embedded slave part for the nerve monitoring module 20, which can easily be further integrated in a monitoring platform for the surgical device 10. The coupling device 21 can be considered as the "slave", built-in part of the nerve monitoring module 20 as opposed to the remote control unit 22 to which it needs to be connected, making up the "master" part, i.e. in charge of generating the electrical signals, while the coupling device 21 is only in charge of transmitting them further onto the bur 1. Therefore, the proposed configuration for introducing nerve monitoring capabilities is not only advantageous from a structural point of view, but also from a logical point of view in terms of overall monitoring architecture integration.

Figure 2:
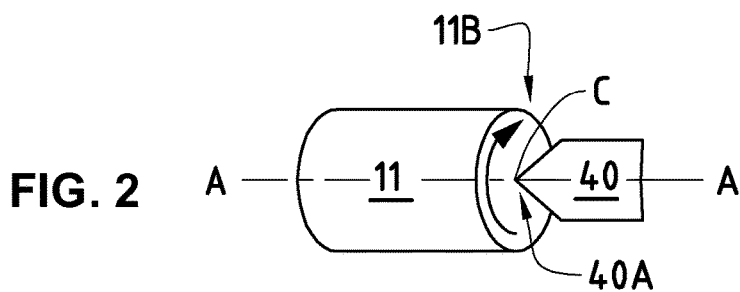
FIG. 2 shows a schematic view illustrating the axial contacting principle used within the framework of the present invention.

As illustrated by FIG. 2, the present invention uses an axial contacting scheme for providing mechanical contact instead of the usual radial sliding contacts known hitherto. The mechanical contacting principle in order to provide galvanic conductivity has been known and used for decades for direct current motors, and one major drawback thereof is the generation of friction, wear (additionally yielding wear particles) and heat, which severely limit the lifetime. Therefore, the goal of the proposed solution is to minimize the rate of wear to achieve a maximal lifetime, while still maintaining high signal transmission quality. The three most important factors which lead to wear are the contact surface, the contact time and the contact force; the provided solution defines an optimal use of all these parameters.

The axial contacting principle providing resistive electrical contact depicted on FIG. 2 shows two contacting elements, namely a rotating shaft 11 and an axial contacting element 4, which are brought into contact with each other along an axial direction, here the rotational axis A-A of the rotating shaft 11. The axial contacting element 4 preferably consists of a component that, in absence of friction, is supposed to exert a mechanical contact force F (represented e.g. in FIG. 3) mainly in the direction of the rotational axis (A-A) of the rotating shaft 11. According to this schematic illustrated example, the axial contacting element is formed by a contacting pin 40, and is provided with a tapered tip 40A in order to provide the sharpest possible tip and therefore to minimize the surface of contact between it and the rear end 11B of the rotating shaft 11, and hence minimize the wear; actually the physical modelling depicted in FIG. 2 would even correspond to a contact point C being a mathematical "single" point of contact, where the disc of the rotating shaft 11 rear end 11B intersects the rotational axis A-A. This corresponds to an ideal situation from the perspective of attrition. Another preferred embodiment is illustrated further by FIG. 6, where the contacting surface G is broader, yet still arranged symmetrically around the rotational axis (A-A) of the rotating shaft 11, and still stretching inside the radius R of its rear end 11B, as explained later.

Moreover, this tip 40A is applied axially preferably into the center of the rotating shaft 11. Arranging the mechanical contact between the rotating shaft 11 and the contacting pin 40 around such a contact point C located on the rotational axis is also very advantageous because the rotation speed along this axis remains close to zero, irrespective of that applied to the rotating shaft 11 by the motor 5. Therefore, it provides the best possible scalability in terms of drilling speeds, up to speeds typically above 100,000 rotations per minute (rpm), while remaining user-friendly (limited heating levels and preserved ergonomics for the surgeon, especially for long usage periods) and while ensuring an acceptable lifetime. This would not be conceivable with a radial contact where the peripheral speed applied on the outer diameter would lead to very high shear forces, instead of the reduced torque levels applied.

In order to ease the cooperation of the contacting pin 40 with the rotating shaft 11 rear end 11B, a recess may be machined at the level of the contact point C, like for example the conical recess 110 illustrated in FIG. 1B. Other geometrical shapes that are also symmetrical around the rotational axis, such as e.g. a spherical shape, could also be considered for this recess 110, that may be optionally filled up with a harder material, i.e. less easily abraded than the one used for the contacting pin 40, so that the lifetime of the rotating shaft 11 is maximized over that of the contacting pin 40. This is preferable because it is usually easier to interchange the contacting pin 40 by merely unscrewing the cable protection cap 17, whereas the rotating shaft 11 part is interlocked with the motor 5 and less accessible inside the casing 14. However, in alternative embodiments where the rotating shaft 11 would be made of one single piece integral with the bur 1, and would need to be interchanged quite often, the material used for the recess 110 could be more abrasion-resistant than the one used for the contacting pin 40. In practice, applying regular stainless steel to the rotating shaft while using a contacting pin 40 made of brass has proven to be suitable to implement the provided solution involving this axial contacting scheme.

As mentioned previously, now that an optimal solution has been found for the mechanical contact, two other parameters may still be considered for further optimization, namely the contact time and the contacting force. However, good electrical contact still needs to be ensured in order to guarantee the transmission of electrical signals. In the following, a preferred embodiment is described which addresses this trade-off problem between further wear optimization and reliable resistive conductivity.

FIG. 3 shows, for the sake of simplification, a schematic bur 1 having a one-piece monobloc rotating shaft 11 stretching from the drilling tip 12 at its distal end 11A on the left side of the figure to its rear end 11B on the right side, which is contacted by a sharp tip, typically a tapered tip 40A of a contacting pin 40 (not illustrated in this schematic drawing) which may be made of a less hard material, i.e. more easily abraded material, than the one of the rotating shaft 11, at least at the contact point C level. This tapered tip 40A through which electrical contact occurs is arranged on a linear actuator 3, that is movable in translation along the rotation axis A-A of the rotating shaft 11, in order to provide only intermittent contact between the coupling device 21 and the rotating shaft 11. Owing to the fact that the physical contact is no longer permanent, but only sporadic, the effect of wearing forces are limited accordingly and in turn the lifetime is consequently improved.

Although not explicitly indicated in FIG. 3, such a linear actuator would be part of the coupling device 21 of the nerve detection module 20, connected to the remote control unit 22 generating two kinds of electrical signals:

Electrical nerve stimulation signals S, and
Electrical pulse signals P

The first type of electrical signals referred to as "S" signals need to be transmitted up to the drilling tip 12 for real-time nerve detection, while the second type of signals "P" are intended to minimize the contact time. Each type of signals are transmitted through dedicated electrical wires pertaining to distinct electrical circuits:

$W_s$ as a first electrical wire for the transmission of the nerve stimulation signal S, and $W_p$ as a second electrical wire for the transmission of the pulse signals P).

Figure 4:
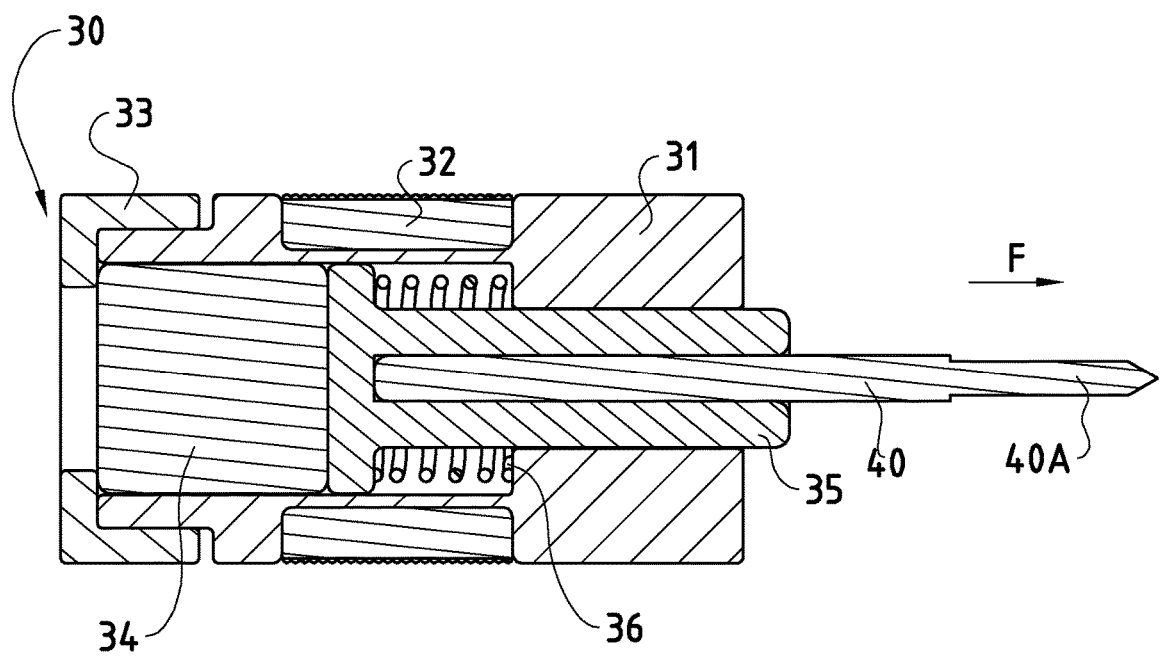
FIG. 4 shows a sagittal cross-sectional view of an electromagnetic linear actuator used in the preferred embodiment of the surgical drilling piece with integrated nerve monitoring as illustrated in FIG. 1B.

Although the first electrical wire $W_s$ is represented schematically only in FIG. 3 to show that electrical contact is required on the sharp tip 40A, in practice an electrical wire could merely be soldered radially on a contacting pin 40 terminated by the tapered tip 40A (e.g. around the plunger 35 of FIG. 4 showing a concrete physical embodiment for the linear actuator 3 as an electromechanical linear actuator 30) to reach this goal. The second electrical wire $W_p$ is wrapped around the linear actuator body, hinting at an electromechanical actuator; however, in order to provide linear displacement, other types of actuators like e.g. piezo-electrical motors and linear DC-servomotors could also be employed.

The linear actuator 3 is designed to carry out a reciprocating linear movement over a travel distance D preferably comprising between 0.5 mm and 2.5 mm, whereby the lower boundary of 0.5 mm can even be reduced to 0.3 mm. The shorter the travel distance D is, the faster the contacting pin 4 can be brought into its working position; therefore, the more efficient it is for providing sporadic contact times. On the other hand, the longer the travel distance D is, the better the electrical insulation is when the linear actuator 3 is in its resting position where no electrical contact is ever supposed to occur. Moreover, it requires less fine adjustment of the relative axial position of the contacting pin 40 with respect to the rear end 11B of the rotating shaft 11 when mounting the coupling device 21 inside the casing 14 (see FIG. 1B). Hence, a trade-off needs to be set for the travel distance D. Moreover, since this travel distance D is directly linked to the power emitted on the control circuit of the linear actuator 3, it cannot therefore be increased to too high levels in order to comply with clinical safety requirements; moreover, it also influences the width of the spacer 15 and adds up to the additional length L (see FIGS. 1A & 1B) of the surgical drill 10. As a result, an average level of around 1.5 mm travel distance D is preferably set according to a preferred embodiment for the present invention for an applied power of 10 W, with an initial spacing of 0.5 mm between the tapered tip 40A and the rotating shaft 11 in a resting position. Since the higher the magnitude of the force applied onto the rotating shaft 11 is, the better is the reliability of the electrical contact, and moreover this magnitude precisely depends on the power applied on the linear actuator, such a configuration has proven to yield a suitable resulting applied force of at least 0.3 Newton on the rear end 11B of the rotating shaft 11, thereby ensuring reliable electrical contact over the whole lifetime of these contacting pieces, even when the surgical drilling device 10 is operated at very high speeds. Ideally, with an optimized system, this force could be reduced to as little as 0.1 Newton.

FIG. 4 shows an exemplary preferred embodiment for the linear actuator 3 as an electromagnetic linear actuator 30, actually corresponding to an enlarged view of the electromagnetic linear actuator 30 represented in FIG. 1B. It comprises a coil 32 wrapped around a case 31 made e.g. of aluminium, and that cooperates with a movable magnet 36 integral with a contacting pin 40 provided with a tapered tip 40A on a stepped extremity portion protruding out of the case 31. The outer diameter of such a preferred complete actuator is preferably only 8 mm, so that it can easily fit into an existing surgical motor casing, while the part of the contacting pin 40 protruding out of the case 31 preferably does not exceed 5-6 mm (4 mm for the stepped extremity portion visible in this figure) in order to provide a very compact design. In addition, this electromechanical actuator 30 is advantageous for implementing an intermittent contact because it allows for fast reaction and thus fast contacting when supplied with adequate electrical power.

Figure 5A:
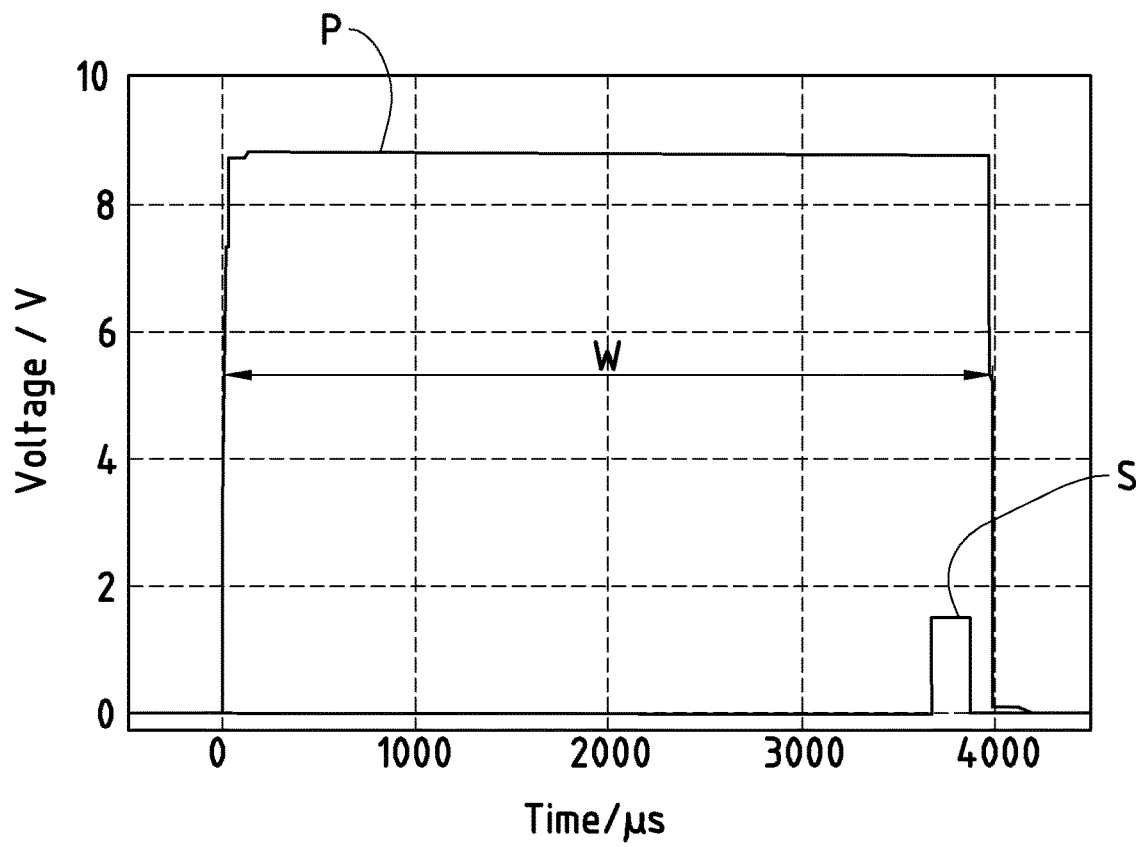
FIGS. 5A and 5B show respectively the electrical pulse pattern transmitted to the coupling device as compared with the electrical nerve stimulation signal, and the transmitted electrical nerve stimulation signal measured on the bur during operation.

The preferred electromechanical linear actuator 30 illustrated in FIG. 4 also comprises a plunger 35 onto which the contacting pin 4 is mounted, and that is pressed by said return spring 36 against a back cover 33 of the case 31. The fact that the contacting pin 40 is spring-mounted onto the plunger 35, which is displaced together with the magnet 34 when the coil 32 is supplied with electrical signals such as the pulses P illustrated on the following FIG. 5A, is beneficial because it helps reduce bouncing effects when the electrical contact is first established; furthermore, this spring-mounted configuration is meant to ensure that the contacting pin 40 can never accidentally come into contact with the rotating shaft 11 in the absence of any activation signal—such as the electrical pulses P—fed to the electromechanical linear actuator 30, even when the surgeon manipulates the surgical device, thanks to the elastic force exerted by the return spring 36 keeping it pushed back. Moreover, the presence of the return spring 36 is also advantageous since it normalizes the magnitude of the force F applied by the contacting pin 4 onto the shaft, which is not only required to remain preferably higher than 0.3 Newtons in order to ensure a good electrical contact, but also desirable so as not to exceed 1 Newton in order not to cause too much wear.

As explained previously in the above description, the present invention tackles the wear issue by defining first an optimized contacting scheme between two elements by minimizing the contact surface and friction forces between them, then it also strives to minimize the contact time and the contact force exerted onto the rotating shaft 11. Explained in the following is how the contact time can be further optimized and which constraints need to be observed in terms of reliability for the transmission of the electrical signal.

FIG. 5A illustrates a comparative diagram showing the shape of electrical nerve stimulation signals S and electrical pulse signals P. The electrical pulse signals P are intended to bring the contacting pin 40 into contact with the rotating shaft 1, so that the electrical nerve stimulation signals sent by the remote control unit 22 can be further transmitted up to the drilling tip 12. A pattern commonly used for electrical nerve stimulation signals S is a pulse of 200 µs repeated at a frequency of 3 Hz; it is precisely the one illustrated on this figure as a rectangular pulse of around 1.5 volts magnitude. The electrical pulse signal P is also of rectangular shape, but lasts around 4 ms (i.e. 4000 µs, materialized by the pulse time window W) and has a magnitude of 8 volts. As a result, the pattern of the nerve stimulation signal S is fully included in the one of the electrical pulse signals P. The reason for this inclusion is twofold: firstly, the greater magnitude of the electrical pulse signal P is due to the contact force requirements which must meet minimal levels in order to guarantee reliable physical and electrical contact; secondly, the time-wise pattern of the electrical pulse signal P must strictly include that of the nerve stimulation signal S, because these latter signals can only be transmitted during a time period when reliable physical contact is ensured, once unwanted rebounds have faded away. In practice, the available time to send nerve stimulation signals S is strictly less than the pulse time window W, due, on the one hand, to the slight inclined slope of the rectangular signal pulse wave, that is never entirely vertical, and most importantly, on the other hand, due to the overall activation time of around 1 to 2 ms of the linear electromechanical actuator 30 in order to establish a reliable electrical contact after the actuator is electrically activated, mainly due to the effective travel time of the plunger and then the rebound phases. More generally speaking, the constraint that needs to be respected by the system is therefore that the pattern of the electrical pulse signal P—i.e. the time windows W it defines and the frequency at which they are repeated—must strictly encompass all sending periods of the electrical signals S with a minimal initial offset of preferably at least 2 ms, so that these sending periods always occur during a stable physical contact time between the rotating shaft 11 and the contacting pin 40, and consequently the transmission of the electrical nerve stimulation signals S can be reliably effected.

According to the preferred embodiment disclosed on FIG. 5A, these constraints are respected by aligning the frequency of the electrical pulse signal P to that of the electrical nerve stimulation signal S, both set equal to 3 Hz, and choosing a pulse time window P significantly larger than that of the stimulation signal S (4000 µs, i.e. 4 ms, compared to 200 µs, that is 20 times more) and also leaving enough time, in this case around 3.7 ms that accounts for more than twice the activation time of the actuator, between the start of the electrical pulse signal P and that of the electrical nerve stimulation signal S, in order to guarantee a stable mechanical contact between rotating shaft 11 and the contacting pin 40. Experience has shown, however, that pulse time windows W of a 3000 µs, i.e. 3 ms, are also suitable for such an electrical stimulation signal S, and it will be understood that other stimulation signals and pulse signal patterns defined accordingly in order to respect the above-mentioned set of constraints would also be applicable without departing from the scope of the present invention.

It can be further appreciated that according to this preferred embodiment, the cumulated time period of all physical contact times $T_c$ during the total operation time $T_o$ is set to less than 1% of a total operation time $T_o$ when the pulse time window W is chosen to be 3 ms (actually the total physical contact time per second is, in this case, strictly less than the sum of all pulse time windows W within one second, that is 3 (Hz)*0.003 s=0.009 s i.e. 0.9% of the time). This of course dramatically reduces the wear on the system. Even when multiplying the width of the pulse window W by two, i.e. increasing it to 6000 µs, i.e. 6 ms, thus yielding a total cumulated contact time $T_c$ of less than 2% of a total operation time $T_o$, excellent results are still provided as compared with a permanent physical contact.

Figure 5B:
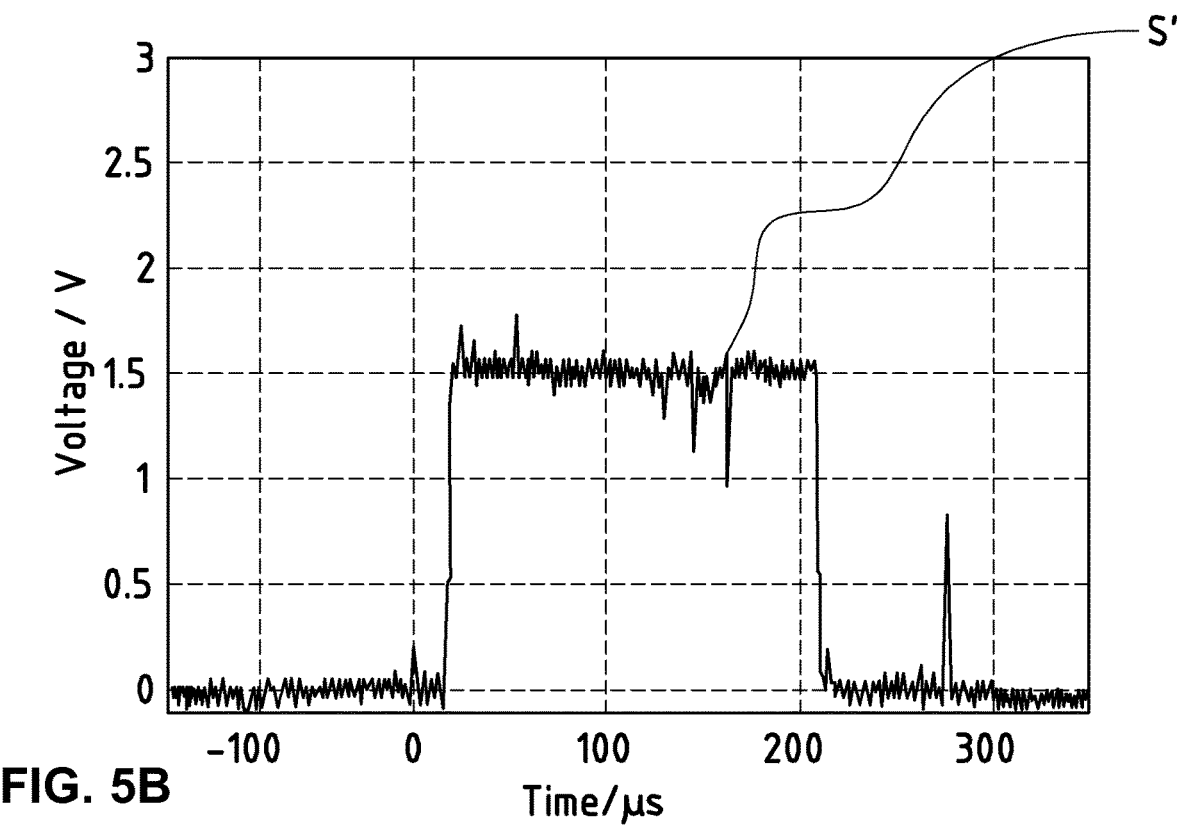

Nevertheless, as shown in FIG. 5B, even under such optimized conditions for minimizing the wear, the reliability of the provided solution in terms of electrical conductivity is not affected, even under high working stress conditions. Indeed, FIG. 5B shows an enlarged view of the transmitted electrical stimulation signal S' of the electrical stimulation signal S shown in FIG. 5A, i.e. a 200 µs pulse of 1.5V magnitude, which is measured directly on the bur 1 while the rotating shaft 11 is rotating at a speed of around 100,000 rpm. It can be appreciated that the signal quality is fully preserved. As a result, the proposed invention offers a solution that not only efficiently minimizes the wear on an integrated nerve monitoring apparatus using mechanical contacting principle, whose lifetime is therewith significantly extended, but it also scales up very well for high speed drilling operations.

These beneficial technical advantages are further obtained through a compact and modular design, that allows the complete surgical drill instrument, including the motor, the drill handpiece and the surgical bur, as shown in FIGS. 1A and 1B (explained at the very beginning of this section), to remain almost identical in their appearance and outer dimension, except for the several millimeters of length extension at the back of the motor. No additional cables are needed either towards the tip of the instrument nor on the handpiece, hence no visual and handling annoyances are to be expected by the surgeon. On the other hand, from a manufacturing perspective, extensive leveraging of available products and parts can additionally be realized.

Figure 6:
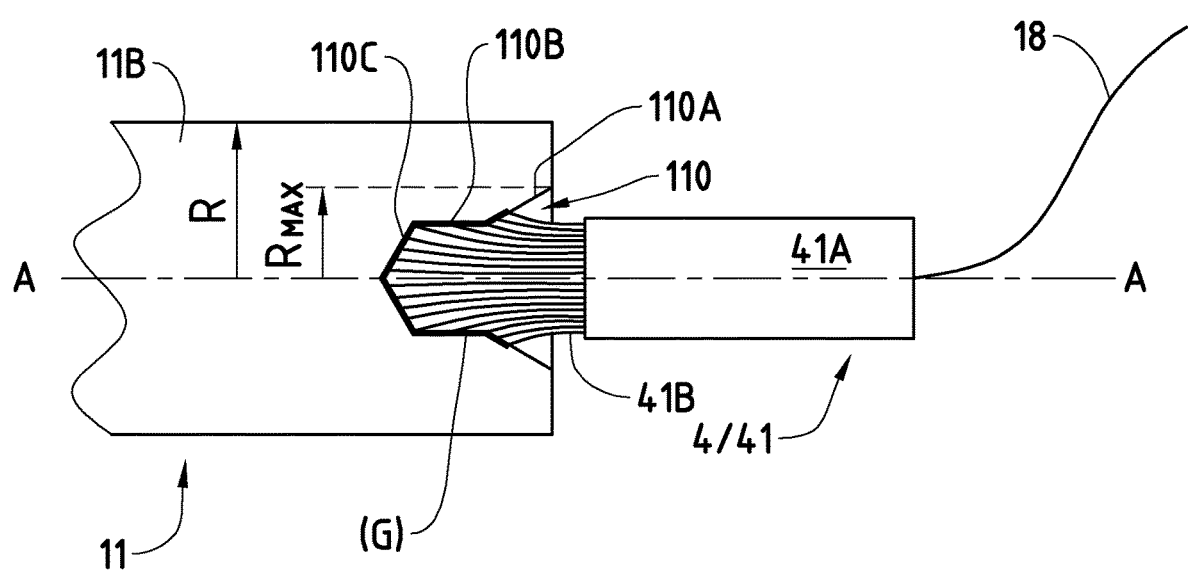
FIG. 6 shows a schematic view illustrating a sagittal cross-sectional view of a multi-wire carbon brush used for the electrical connexion between the bur and the nerve monitoring module, according to another preferred embodiment for the present invention.

FIG. 6 shows another preferred embodiment for coupling the bur 1 to the nerve monitoring module 20, involving a carbon brush 41 for electrical connexion with the rotating shaft 11 as an axial contacting element 4 instead of a contacting pin 40. The left part of FIG. 6 actually corresponds to an enlarged view of the rear end 11B of the rotating shaft 11 of the bur 1, fitted with a tapered recess 110 comprising three different sections: a tapered opening 110A of a conical shape, a cylindrical middle part 110B, and a tapered end 110C acting as a stop. This form is best suited to fit in the wires 41B of a multi-wire carbon brush 41, that are hence best guided into the recess 110; however, other shapes symmetrically arranged around the rotational axis (e.g. purely cylindrical or made of one single tapered section) could also be considered. The multi-wire carbon brush otherwise preferably comprises a body 41A connected to the connexion cable 18 providing electrical connectivity to the remaining of the nerve monitoring module 20 such as the remote control unit 22 (not illustrated).

As it can be appreciated in view of FIG. 6, the contact surface G, between the rotating shaft 11 and the axial contacting element 4 of the coupling device 21, formed here by the carbon brush 41 stretching substantially centrally along the rotational axis (A-A) of said rotating shaft 11, is fitted into the recess 110 and stretches along almost all of its three different sections 110A,110B,110C, whereby all of the contact points making up the contact surface G, highlighted overall in bold in this Figure, are comprised inside a volume defined inside the cylinder having a radius R of the rear end 11B of the rotating shaft 11. Hence, the radial speed at the level of these contact points is minimized, as compared to a radial sliding on top of this cylinder as taught in the prior art. Accordingly, the wear is reduced while better compactness is ensured. More specifically, since it is sought, in the frame of the present invention, to improve the wear, it can be appreciated that the contact surface G is preferably arranged inside a smaller radius Rmax as compared to the one of the rear end 11B, This smaller radius Rmax corresponds to the one at the end of the tapered opening 110A section of the recess 110. According to the preferred embodiment depicted in FIG. 6, the contact surface G could encompass part or all of any sections 110A, 110B, 110C of the recess 110, or any combination thereof.

In comparison with the previous embodiment using a contacting pin 40 as an axial contacting element 4, this design illustrated on FIG. 6 involving a carbon brush 41 provides a much larger contact surface G instead of a single contact point C, and hence a more reliable galvanic contact for electrical conductivity, being at least more robust with respect to vibrations or shocks than the one provided by a single point of contact. On the other hand, the wearing is not affected dramatically thanks to the fact that the contact surface G is still arranged as close as possible to the center, i.e. the rotation axis A-A, and that the softness of the carbon wires 41B also soften the contact force applied. Yet a significant advantage of this carbon brush 41 design is that it is much easier to implement, thanks to the considerably reduced constraints in terms of both radial positioning of the axial contacting element 4, along the rotation axis A-A, where a small play can now be tolerated, as well as the axial positioning along this very same rotation axis A-A, since no more contact forces are to be exerted e.g. by a spring and no more intermittent contact is required in order to minimize the wear. As a result, the compactness of this design is also positively affected, with a significant amount of space spared behind the rear end 11B of the rotating shaft 11 in this configuration. Thus, the additional length (i.e. the added length L illustrated on FIG. 1A) can be restricted to a minimal level, not exceeding a couple of millimeters.

Although in an ideal case, the carbon brush 41 is supposed to stretch centrally along the rotational axis (A-A) of said rotating shaft 11, and the carbon wires of the carbon brush 41 to be arranged fully symmetrically around this rotational axis (A-A), so that in turn the contact surface G is also arranged symmetrically around this rotational axis A-A of the rotating shaft 11, in practice according to this preferred embodiment it is no more required that the carbon brush 41 is precisely aligned with respect to the rotational axis (A-A), so that there may be a radial offset or a slight inclination with respect to it, without any prejudice to the overall performances of the system. Hence, since it cannot be guaranteed either that all the carbon wires are arranged symmetrically around this rotational axis (A-A), it has been recited that the carbon brush 41 stretches preferably substantially centrally along the rotational axis (A-A), while the contact surface G is also arranged substantially symmetrically around this very same axis.

Without departing from the scope of the present invention, further alternative embodiments still pertaining to the same axial contacting scheme could be considered, wherein the contact surface G would be e.g. comprised on a plane perpendicular to the rotation axis A-A, i.e. where no recess 110 would be arranged at the rear end 11B of the rotating shaft 11, or with a carbon brush 41 deprived of any soft wire, but made of an integral carbon cylinder body, directly applied to the rear end 11B of the rotating shaft 11, irrespective of whether this shaft is provided with a recess 110 or not. Moreover, the "male type" portions and "female type" portions, such as the contacting pin 40 or carbon brush 41, could be arranged on any of the rotating shaft 11 or the coupling device 21. Preferably also, the wearing generated will be set so as not to require frequent replacements of the axial contacting elements 4, but that their lifetime is aligned to the one of the surgical device as a whole, in order not to demand the surgeon to demount and remount the surgical drill 10 at any time for internal pieces replacement purposes.

Although the preferred embodiments of the described nerve monitoring system combined with a fast spinning drill described in the foregoing especially focuses on ENT surgeries including parotid gland surgery, thyroid surgery or cochlear implant surgery, it can be appreciated that this embodiment is given by way of example only and should not be understood as limiting for the conferred scope of protection. ENT is indeed only one of the numerous fields of surgery the proposed system could be applied to; other fields of application such as orthopedic surgeries of the spine, e.g. in cases of scoliosis, could also be considered, as well as also potentially odontic surgeries.

REFERENCES LIST

10 Surgical drill
1 Bur
11 Rotating shaft
11A Distal end
11B Rear end (proximal end)
110 Recess
110A Tapered opening
110B Cylindrical middle part
110C Tapered end
12 Drilling tip
13 Handpiece part
14 Casing
14B Back end
15 Spacing ring
151 Central opening
16 Bearings
17 Cable protection cap
18 Connexion cable
20 Nerve monitoring module
21 Coupling device (built-in part=plug including guiding means+actuator)
22 Remote control unit
3 Linear actuator
30 Electromagnetic linear actuator
31 Case
32 Coil
33 Cover
34 Magnet
35 Plunger
36 Spring
4 Axial contacting element
40 Contacting pin
40A Tip of the pin
41 Carbon brush
41A Carbon brush body
41B Carbon brush wires
5 Motor
6 Axial guiding means (plugged onto ring casing ring 15)
A-A Rotational axis of the shaft
C Contact point
D Travel distance of the actuator
F Contact force applied G Mutual electrical contact surface between the rotating shaft and the contacting element
R Radius of the rear end 11B of the rotating shaft
Rmax Smaller radius fitting the mutual electrical contact surface G
P Electrical pulse signal
L Added length
S Electrical nerve stimulation signal
S' Transmitted electrical nerve stimulation signal
Tc Cumulated time period of physical contact
To Overall time of operation
W Pulse time window for generating physical contact
Ws First electrical wire for the transmission of the nerve stimulation signal S
Wp Second electrical wire for the transmission of the pulse signal P

The invention claimed is:

1. Surgical drilling device with integrated nerve monitoring capabilities comprising a bur that is fitted with a drilling tip and is actuated in rotation by connection to a front end of a rotating shaft driven by a motor, wherein said rotating shaft is electrically connected at an opposite, rear end thereof to a coupling device of a nerve monitoring module comprising an axial contacting element for the transmission of electrical nerve stimulation signals through a concave contact surface stretching inside a radius of a face of said opposite, rear end of said rotating shaft.

2. The surgical drilling device of claim 1, wherein said contact surface between the coupling device and the rotating shaft is arranged substantially symmetrically around a rotational axis of said rotating shaft and stretches inside a smaller radius as compared to said radius of said face of said rear end of said rotating shaft.

3. The surgical drilling device of claim 2, wherein said contacting element is a contacting pin made of metal or a carbon brush stretching substantially centrally along the rotational axis of said rotating shaft.

4. The surgical drilling device of claim 3, wherein said axial contacting element is a contacting pin, and wherein the rotating shaft is made of a material harder than that of said contacting pin.

5. The surgical drilling device according to claim 1, wherein the rotating shaft is provided with a central recess at the face of the rear end thereof, into which said contacting surface is fitted.

6. The surgical drilling device according to claim 5, wherein said central recess has a substantially tapered shape, and wherein said contacting surface is wiped by a plurality of carbon wires of a carbon brush.

7. The surgical drilling device according to claim 1, wherein said coupling device comprises a linear actuator displaceable along a rotational axis of said rotating shaft.

8. The surgical drilling device according to claim 7, wherein said linear actuator is an electromagnetic linear actuator comprising a coil wrapped around a case cooperating with a movable magnet, wherein said magnet is integral with the contacting pin.

9. The surgical drilling device according to claim 8, further comprising a return spring and a plunger onto which said contacting pin is mounted, wherein said plunger is pressed by said return spring against a back cover of said case.

10. The surgical drilling device according to claim 1, wherein said coupling device is modularly mounted inside a casing accommodating said motor, and is fitted at a back end of said casing under a removable cable protection cap.

11. System for operating a surgical drilling device according to claim 1, wherein the nerve detection module further comprises a remote control unit that is configured to send electrical pulse signals to said coupling device for generating intermittent electrical contact between said coupling device and said rotating shaft.

12. The system for operating a surgical device according to claim 11, wherein said remote control unit also sends electrical nerve stimulation signals, and wherein a pattern of said electrical pulse signals defines time windows allowing for the transmission of said electrical nerve stimulation signals.

13. The system for operating a surgical device according to claim 11, wherein a cumulated time period of all physical contact times during a total operation time is set to less than 2% of the total operation time.

14. The system for operating a surgical device according to claim 11, wherein said coupling device is a linear actuator set to travel over a distance within a range of 0.3 mm and 2.5 mm by said electrical pulse signals.

15. The system for operating the surgical device according to claim 11, wherein said coupling device comprises a contacting pin, wherein said electrical pulse signals are set to urge said contacting pin axially against said rotating shaft with a force of a magnitude of at least 0.3 Newtons.

16. Surgical drilling device with integrated nerve monitoring capabilities comprising a bur that is fitted with a drilling tip and is actuated in rotation by connection to a front end of a rotating shaft driven by a motor, wherein said rotating shaft is electrically connected at an opposite, rear end thereof to a coupling device of a nerve monitoring module comprising an axial contacting element for the transmission of electrical nerve stimulation signals through a contact surface stretching inside a radius of a face of said opposite, rear end of said rotating shaft, wherein said contact surface is fitted inside a central recess formed in the face of said opposite, rear end of the rotating shaft.

17. Surgical drilling device with integrated nerve monitoring capabilities comprising a bur that is fitted with a drilling tip and is actuated in rotation by a rotating shaft driven by a motor, wherein said rotating shaft is electrically connected at a rear end thereof to a coupling device of a nerve monitoring module comprising an axial contacting element for the transmission of electrical nerve stimulation signals through a contact surface stretching inside a radius of said rear end of said rotating shaft, wherein said coupling device comprises a linear actuator displaceable along a rotational axis of said rotating shaft.

18. The surgical drilling device according to claim 17, wherein said linear actuator is an electromagnetic linear actuator comprising a coil wrapped around a case cooperating with a movable magnet, wherein said magnet is integral with the contacting pin.

19. The surgical drilling device according to claim 18, further comprising a return spring and a plunger onto which said contacting pin is mounted, wherein said plunger is pressed by said return spring against a back cover of said case.

* * * * *